(12) United States Patent
Artsyukhovich et al.

(10) Patent No.: US 7,150,530 B2
(45) Date of Patent: Dec. 19, 2006

(54) VARIABLE SPOT SIZE ILLUMINATOR HAVING A ZOOM LENS

(75) Inventors: Alexander N. Artsyukhovich, Aliso Viejo, CA (US); Bruno X. Lassalas, Irving, CA (US); T. Scott Rowe, Dana Point, CA (US); Mark Fink, Tucson, AZ (US); Robert E. Fischer, Westlake Village, CA (US)

(73) Assignee: Alcon, Inc., Hunenberg (CH)

( * ) Notice: Subject to any disclaimer, the term of this patent is extended or adjusted under 35 U.S.C. 154(b) by 611 days.

(21) Appl. No.: 10/442,740

(22) Filed: May 21, 2003

(65) Prior Publication Data

US 2004/0233388 A1 Nov. 25, 2004

(51) Int. Cl.
*A61B 3/10* (2006.01)

(52) U.S. Cl. .................. 351/216; 351/211; 351/221; 362/250; 362/268; 359/210

(58) Field of Classification Search ............... 351/205, 351/211, 216, 221; 606/4–6, 16–19; 362/250, 362/268, 280, 281; 359/210, 362, 642–651; 600/160, 163, 167, 168
See application file for complete search history.

(56) References Cited

U.S. PATENT DOCUMENTS 4,476,519 A * 10/1984 Hayamizu .................. 362/554
4,538,608 A * 9/1985 L'Esperance, Jr. ............. 606/3
4,628,416 A * 12/1986 Dewey ....................... 362/553
4,676,594 A    6/1987 Presby
4,934,787 A    6/1990 Ichimura et al.
4,974,930 A   12/1990 Blyler, Jr. et al.
5,171,242 A   12/1992 Dewey et al.
5,207,673 A    5/1993 Ebling et al.
5,336,216 A *  8/1994 Dewey ......................... 606/4
5,342,351 A    8/1994 Blaha et al.
6,004,314 A * 12/1999 Wei et al. .................... 606/12
6,142,988 A * 11/2000 Strahle et al. ................. 606/4
6,172,813 B1 *  1/2001 Tadic-Galeb et al. ....... 359/618
6,473,236 B1 * 10/2002 Tadic-Galeb et al. ....... 359/618
6,648,876 B1 * 11/2003 Murakami .................... 606/4
6,652,511 B1 * 11/2003 Tomita ........................ 606/4
6,680,803 B1 *  1/2004 Schultz et al. .............. 359/649

FOREIGN PATENT DOCUMENTS

EP       0 960 609 A1 *  1/1999

* cited by examiner

*Primary Examiner*—A. Farah
(74) *Attorney, Agent, or Firm*—Jeffrey S. Schira

(57) ABSTRACT

The present invention provides variable spot size illuminators that provide a light spot on a treatment plane by utilizing a zoom lens to direct light received from an image of a light source formed on an intermediate image plane onto the treatment plane. The zoom lens allows varying the size of the treatment spot while ensuring that the treatment spot exhibits parfocality. An illuminator of the invention can be utilized for performing a number of ophthalmic surgical procedures, such as, photocoagulation, transpupillary thermal therapy, and photodynamic therapy.

19 Claims, 4 Drawing Sheets

VARIABLE SPOT SIZE ILLUMINATOR HAVING A ZOOM LENS

BACKGROUND OF THE INVENTION

The present invention relates generally to variable spot size illuminators, and more particularly, to such illuminators that can provide a homogeneous illumination spot whose size can be continuously varied while exhibiting parfocality.

A number of ophthalmic surgical procedures performed on a patient's retina require illuminating a selected portion of the retina with an illumination spot, typically provided by a laser, having a desired size. For example, in one such surgical procedure, known as photocoagulation, a laser light spot is directed to a selected portion of a patient's retina to cause coagulation of the illuminated tissue by generating heat. Photocoagulation can be employed, for example, to seal leaky blood vessels, destroy abnormal blood vessels, or heal retinal detachment.

In another ophthalmic surgical procedure, commonly known as photodynamic therapy, an agent, which is inert in the absence of light activation, is initially administered intravenously to the patient. Subsequently, abnormally highly vascularized retinal tissue containing the agent is illuminated with laser light having a selected wavelength to activate the agent. The activated agent can destroy the abnormal tissue or have other beneficial therapeutic effects.

In such procedures, it is generally advantageous that the light intensity over the illuminated area be substantially uniform, and remain stable for the illumination period. Further, the size of the illumination spot may need to be varied while ensuring that the location of the spot remains focused on the patient's retina. In practice, a surgeon typically employs an illuminator for performing an ophthalmic procedure together with an observation system, such as a slit lamp microscope or an indirect ophthalmoscope, that allows the surgeon to observe and treat a desired area. The focus associated with the illuminator should coincide with the focus associated with the observation system so that the surgeon can simultaneously observe and treat a desired area. That is, it is desirable that the illuminator and the observation system be parfocal. In general, two independent optical systems with foci that lie on the same focal plane are known as being parfocal, and this relationship is known as parfocality. Traditional variable spot size illuminators provide variable magnification of a light spot formed on a treatment plane, e.g., a patient's retina, by moving one or more lenses in a manner that causes the movement of the illuminator's focal plane. Thus, in traditional variable spot size illuminators, although the illuminator may be parfocal with an observation system at one spot size, the parfocality is lost at a different spot size. This in turn requires the surgeon to refocus or re-accommodate at different spot sizes, and further adversely affects the image quality, e.g., sharpness of focus, of the treatment spot.

Further, a patient undergoing laser treatment is not entirely motionless. In fact, the patient's head typically move, for example, back and forth during the treatment procedure. In most conventional slit lamp microscopes, the surgeon can displace the slit lamp's observation and treatment optics to follow the patient's motion in order to ensure that the patient's retina remains aligned and in-focus relative to the aiming beam. While a patient's sideways displacements can be readily tracked through the displacement of the aiming beam on the retina, the patient's displacement along the optical axis, that is, towards and away from the observation/treatment optics, can typically only be tracked by the surgeon's perception of the sharpness of the focus of the retinal image and of the aiming beam spot. Such perceived sharpness of focus is, however, often misleading because of differences in depth of focus at different magnifications of the observation system, and variability in the ability of different surgeons to accommodate. This can result in a considerable variation of the treatment beam's spot size, and consequently the treatment beam's intensity, on the retina over the range of the slit lamp's depth of focus.

Accordingly, there is a need for medical illuminators that can provide a spatially homogeneous illumination spot on a selected portion of a patient's retina.

There is also a need for such illuminators that can allow readily adjusting the size of the illumination spot on a selected portion of the patient's retina.

Moreover, there is a need for such illuminators that allow adjusting the size of an illumination spot while ensuring that the illuminator's focal distance, known also as the working distance, remains substantially constant, thereby maintaining parfocality with other optical systems coupled to the illuminator. In other words, there is a need for illuminators that exhibit "spot size variation parfocality."

Further, there is a need for medical illuminators in which the spot size and the intensity profile of a treatment laser remain substantially stable, e.g., they vary by less than about 10%, over a selected distance (e.g., mm) from the laser's focal plane. In other words, there is a need for medical illuminators that exhibit "observation depth of focus parfocality" in which the treatment conditions are reasonably stable through the entire range of the observation system's depth of focus.

SUMMARY OF THE INVENTION

The present invention provides variable spot-size illuminators that image a radiation source on a treatment plane, typically in the form of a homogeneous illumination spot, whose size can be varied while ensuring parfocality. The terms "light" and "radiation" are herein utilized interchangeably. In particular, the term "light" is intended to refer to not only the visible portion of the electromagnetic spectrum, but also to the portions of the spectrum that lie beyond the visible range, for example, the infrared and the ultraviolet portions. In one aspect, a variable spot size illuminator of the invention includes a radiation source, and a focusing lens system optically coupled thereto that generates an image of the radiation source on an intermediate image plane. The generation or formation of an image on a plane is herein intended to encompass image formation on the plane as well as image formation in close proximity of the plane, for example, within a few millimeters (e.g., 2–3 mm) of the plane. A zoom lens system disposed between the intermediate plane and a treatment plane re-images the intermediate image at a selected size on the treatment plane, or in close proximity thereof, e.g., within mm of the treatment plane. The zoom lens can have at least one fixed lens and two movable lenses that can be adjustably positioned relative to the fixed lens so as to vary a size of the light spot formed on the treatment plane while ensuring that the image remains on the treatment plane at any selected spot size.

In a related aspect, the zoom lens system includes a fixed, focusing, convergent lens positioned at a substantially fixed distance relative to the intermediate plane. The fixed, focusing convergent lens receives light from a homogeneous intermediate image, and refracts the light towards a movable divergent lens. The divergent lens is movable relative to the fixed focusing lens, and generates a plurality of divergent light rays. The zoom lens further includes a movable convergent objective lens that is likewise movable relative to the fixed focusing lens. The lenses of the zoom lens assembly cooperate to re-image the homogeneous intermediate plane image onto the treatment plane, thereby preserving homogeneous light distribution at the treatment site.

In a related aspect, the radiation source, which can be a laser operating at a selected wavelength, is coupled to an optical fiber that delivers light from the source to the focusing lens system. The optical fiber can include a flexible long fiber with a small core, for example, a diameter of about 100–200 microns, and a short internal fiber with a large core, for example, a diameter of about 200–400 microns, that provides a higher number of fiber modes that result in minimizing speckle pattern in its light output. The internal optical fiber can include, or can be coupled to, a mode scrambler that mixes energy among a plurality of fiber modes in order to generate a spatially homogenized beam for illuminating the focusing lens system. Such a mode scrambler will also significantly lower the laser spot's intensity variations that can result from mode competition caused by the external fiber motion.

In another aspect, a variable spot size illuminator of the invention as described above further includes a beam splitter disposed between the light source and the intermediate plane to direct a portion of a light beam generated by the light source to the focusing lens system, and to direct another portion of the light beam to a photodetector that measures the intensity of this portion of the light beam. The intensity of the light beam can be distributed between these two portions such that the portion directed to the focusing lens system has about 95% to 99.5% of the original beam intensity, and the portion directed to the detector has about 0.5% to about 5% of the original beam intensity. Further, the photodetector can be calibrated based on the relative intensities of the two beams so as to provide a direct measure of the intensity of the beam directed to the focusing lens system.

In another aspect, a variable spot size illuminator of the invention can include another radiation source for providing an aiming beam, and another focusing lens system for imaging the aiming beam onto the intermediate plane. The aiming beam can be utilized for accurate positioning of the treatment beam onto a selected portion of the treatment plane. A variety of light sources can be employed for generating the aiming beam. For example, a laser operating at a wavelength detectable by human eye, for example, a diode laser, can generate the aiming beam.

In a related aspect, an axicon can be disposed between the light source providing the aiming beam and the intermediate plane in order to transform the aiming beam from one having a disk-like cross sectional intensity profile into one that forms an annular pattern at the intermediate image plane. The focusing lens system positioned between the aiming light source and the intermediate plane thus provides an image of the aiming beam in the form of a ring of light on the intermediate plane, which can then be imaged onto the treatment plane for aligning the treatment beam. In particular, the image of the treatment beam on the intermediate plane can be adjusted relative to the aiming beam on that plane in order to coaxially align the two beams. For example, the aiming beam can be steered, e.g., by moving one or more turning mirrors or other optical elements, such that the annular aiming beam's image outlines the perimeter of the treatment beam's image on the intermediate and treatment planes.

In other aspects, the invention provides a variable spot size illuminator that provides a light spot on a treatment plane with parfocality. Similar to the illuminators of the invention described above, such an illuminator includes a radiation source that can generate, for example, a beam of light, and a focusing lens system that is optically coupled to the light source in order to generate an image of the light beam on an intermediate plane. The illuminator can further include a zoom lens disposed between the intermediate plane and a treatment plane to direct a beam of light received from the intermediate image onto the treatment plane in order to form a treatment light spot thereon. The zoom lens is designed such that a diameter of the beam directed by the zoom lens towards the treatment plane on any plane within a pre-defined distance of the treatment plane (e.g, mm) varies from the diameter of the light spot on the treatment plane by less than a pre-defined value, e.g., by less than about 10 percent. Such small variations of the treatment spot size as a function of distance from the treatment plane allow the illuminator to remain parfocal with an observation system (i.e., to exhibit "observation depth of focus parfocality") even as the patient's head, and consequently the patient's retina, move over a distance in a range of a few millimeters. Further, the zoom lens allows adjusting the size of the treatment spot within a pre-defined range without disrupting parfocality, i.e., exhibits "spot size variation parfocality."

In another aspect, a variable spot size illuminator of the invention can include a feedback system for collecting at least a portion of radiation originating from the treatment spot, herein referred to as feedback radiation, in response to illumination. The feedback system can include an analyzer that analyzes the feedback radiation to extract selected parameters, e.g., temperature, associated with the treatment spot. The feedback system can further include an electronics control module coupled to the light source providing the treatment beam and the analyzer so as to provide a feedback path between these two components. This feedback path can transmit feedback signals from the analyzer to the light source in order to adjust selected parameters of the light source, e.g., power, in response to the analysis of the feedback radiation.

In a related aspect, the zoom lens in a variable spot size illuminator as described above directs the light beam received from the intermediate image towards the treatment plane such that a beam waist is formed at a distance less than a pre-defined value, e.g., at a distance less than about 5 mm, from the treatment plane, to ensure "observation depth of focus parfocality."

Further understanding of the invention may be obtained from the following detailed description in conjunction with associated drawings that are described briefly below.

DETAILED DESCRIPTION

The present invention provides a variable spot-size illuminator that images a treatment beam on an intermediate plane, and utilizes a zoom lens system to re-image the image formed on the intermediate plane onto the treatment plane at a selected magnification. The illuminator further includes an annular aiming beam that can propagate coaxially with the treatment beam to allow positioning the treatment beam on an outlined portion of an illumination/treatment plane.

Figure 1:
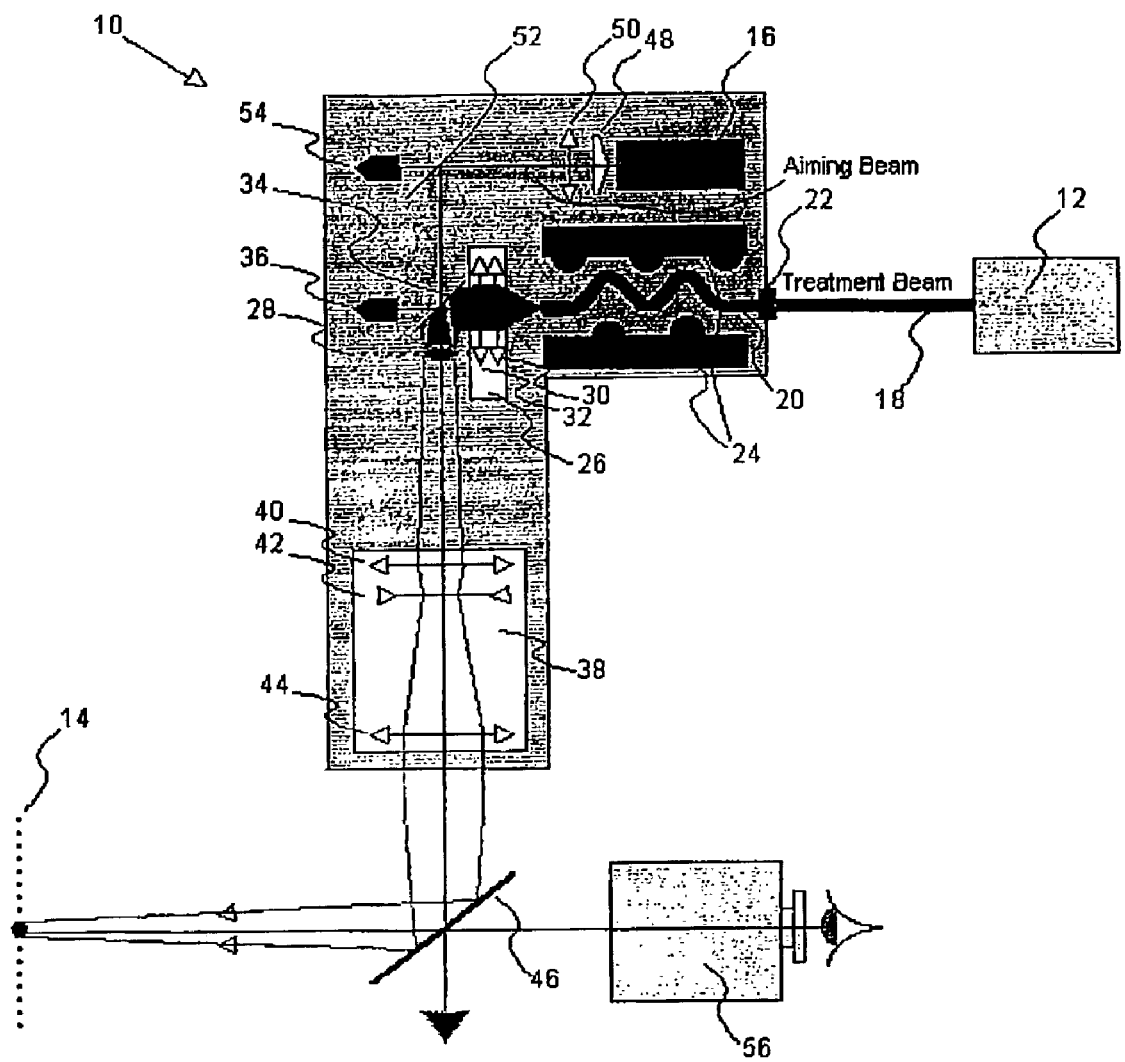
FIG. 1 schematically illustrates an exemplary variable spot size illuminator according to the teachings of the invention.

More particularly, FIG. 1 schematically illustrates an exemplary variable spot size illuminator 10 according to the teachings of the invention that employs a treatment light beam provided by a treatment radiation source 12, such as a laser, to generate a treatment spot on a treatment plane 14, as described in detail below, and further employs an aiming beam provided by an aiming light source 16, e.g., another laser operating at a different wavelength, to direct the treatment spot to a desired location on the treatment plane.

The treatment light source 12, which can be a laser providing light at a selected wavelength, is optically coupled to an external optical fiber 18 that delivers the light emitted by the source 12 to an internal optical fiber 20. A connector 22 optically couples the external fiber 18 to the internal fiber 20. A variety of treatment light sources can be utilized in the practice of the invention. For example, the radiation source 12 can be a laser providing radiation at a wavelength in a range of about 700 nm to about 900 nm suitable for retinal photodynamic therapy. Alternatively, the radiation source can be a laser providing radiation at a wavelength that is suitable for performing retinal photocoagulation, e.g., laser generating green light at a wavelength of 532 nm. In another application, the radiation source can be a laser operating at a wavelength of 810 nm for use in performing transpupillary thermal therapy (TTT).

Although two fibers are utilized in this exemplary illuminator to direct light from the light source 12 to other components of the illuminator, those having ordinary skill in the art will appreciate that a single fiber can be employed for this purpose, or alternatively, free space propagation of the treatment beam can be employed to direct light from the treatment light source 12 to other components.

The internal fiber 20 is passed through a fiber mode scrambler 24 that advantageously mixes optical energy among various modes of the internal fiber 20 so as to spatially homogenize the light beam, thereby producing a homogeneous light beam having a relatively uniform intensity profile over a portion of a plane perpendicular to the direction of propagation. A homogeneous distribution of radiation as used herein refers to a radiation intensity profile that varies by less than about 10 percent around an average value over a selected illuminated area, and falls sharply to vanishing values at the boundaries of this area. The excitation of many modes, and preferably all modes, of the internal fiber 20 also lowers light intensity variations that can occur as a result of mode competition that can be caused by the motion, e.g., bending, of the external fiber. The internal fiber 20 then launches the homogeneous beam towards a focusing lens system 26 that images the beam onto an intermediate image plane 28. A variety of fiber mode scramblers known in the art can be utilized in a variable spot size illuminator of the invention. For example, U.S. Pat. No. 4,934,787, herein incorporated by reference, describes a mode scrambler that can convert the mode distribution of light transmitted through an optical fiber into a stationary distribution. Details regarding other exemplary mode scrambling arrangements can be found in U.S. Pat. No. 4,974,930 and U.S. Pat. No. 4,676,594, both of which are herein incorporated by reference.

The output beam generated by the internal optical fiber 20 can have a disk-like cross section having a relatively uniform intensity over the illuminated area that falls off rapidly to vanishing values beyond the perimeter of this area. Such a light distribution profile is herein referred to as a flat top distribution. In some embodiments, the disk-like cross-section has a diameter in a range of about 200 μm (microns) to about 400 μm (microns), and more preferably, in a range of about 200 μm (microns) to 300 μm (microns).

With continued reference to FIG. 1, the exemplary focusing lens system 26 is formed of an objective lens 30 and a plano-convex lens 32 that cooperatively image the homogeneous beam received from the internal fiber 20 onto the intermediate image plane 28. The diameters and focal lengths of the lenses 30 and 32 can be selected to suit a particular application of the illuminator. For example, in some embodiments, the objective lens 30 can have a focal length ($F_{30}$) in a range of about 5 mm to 50 mm, and more preferably in a range of about 10 mm to about 20 mm, while the plano-convex lens 32 can have a focal length ($F_{32}$) in a range of about 5 mm to about 50 mm. In general, the focal lengths of the objective lens 30 and the plano-convex lens 32 together with locations of these lenses relative to the output of the internal fiber 20 and the intermediate image plane 28 can be selected so as to obtain a desired magnification (M1) for the image formed on the intermediate plane. For example, in some embodiments of the invention, a magnification (M1) in a range of about 1× to about 10×, and more preferably, in a range of about 1× to 5×, are employed.

Figure 2A:
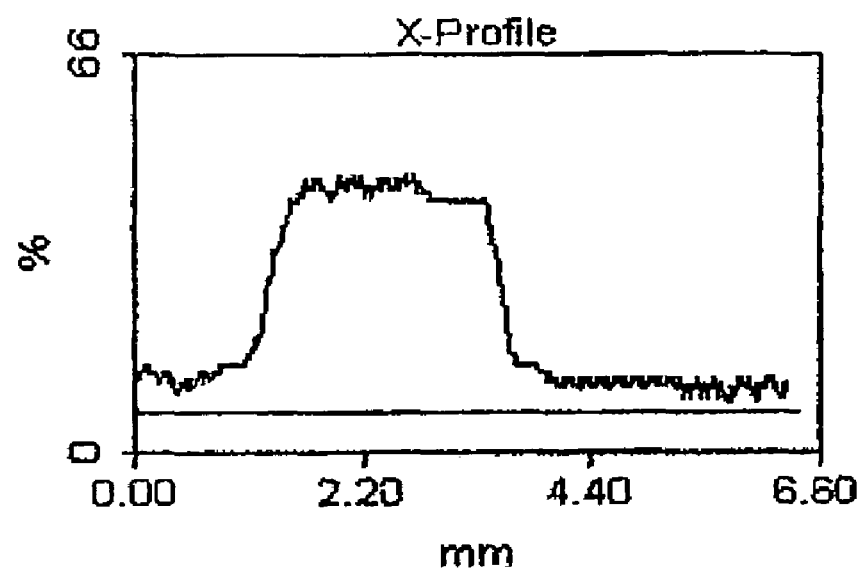
FIG. 2A depicts an experimentally measured flat-top intensity profile corresponding to an image of a treatment beam on an intermediate image plane, in an illuminator of the invention, along a selected dimension, referred to as x-dimension, in the intermediate image plane.
Figure 2B:
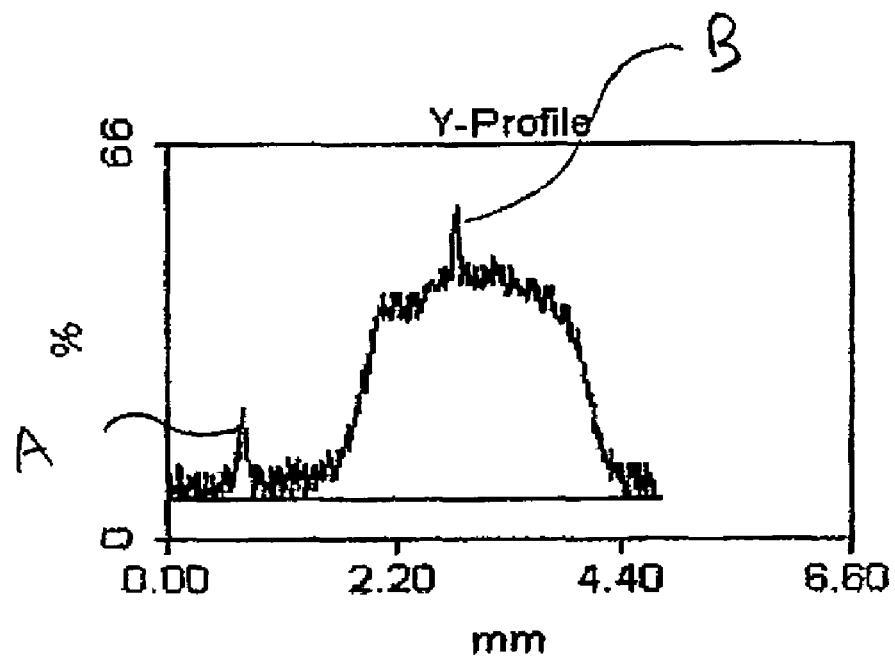
FIG. 2B depicts an experimentally measured flat-top intensity profile corresponding to the intermediate image presented in FIG. 2A measured along a dimension, referred to as y-dimension, perpendicular to the x-dimension, and further depicts cross-sectional intensity profile of an annular beam that is offset from the treatment beam for illustration purposes.

The image of the treatment beam formed on the intermediate plane has preferably a flat top intensity distribution profile. By way of example, FIG. 2A illustrates an experimentally measured intensity distribution, along a horizontal axis (x-axis) in the intermediate plane 28, corresponding to an image of an output end of internal fiber 20 formed on that plane with magnification M1. And FIG. 2B illustrates an experimentally measured intensity distribution, along a vertical axis (y-axis) in the intermediate plane 28, corresponding to an image of an output end of internal fiber 20 formed on the intermediate plane 28 with magnification M1. The illustrated intensity profiles in both directions are substantially uniform over a range of a few millimeters, and fall off abruptly to vanishing values beyond this range. In other words, the image exhibits a flat top intensity distribution. Two intensity peaks A and B visible in FIG. 2B correspond to cross-sectional intensity profile of an aiming beam, described in detail below, that is offset from the treatment beam in this exemplary illustration for clarity.

Referring again to FIG. 1, in this exemplary embodiment, a beam splitter 34 is disposed between the focusing lens system 26 and the intermediate image plane 28 to reflect a portion of the treatment beam from its initial propagation direction onto a substantially perpendicular direction towards the intermediate image plane 28. The beam splitter 34 transmits another portion of the beam, having a substantially lower intensity than the first portion, onto a photodetector 36 that measures the intensity of the transmitted portion. In this exemplary embodiment, the beam splitter 34 reflects approximately 99 percent of the incident treatment beam onto the intermediate image plane 28, and transmits the remainder of the incident beam onto the photodetector 36. Those having ordinary to skill in the art will appreciate that the ratio of the reflected to the transmitted light by the beam splitter 34 can be different than that described above. In fact, any ratio suitable for a particular application can be utilized. The use of the beam splitter 34, in conjunction with forming intermediate images of the aiming beam and the treatment beam, allows utilizing an aiming beam and a treatment beam that exhibit drastically different light intensity distributions, e.g., a ring and a flat top distribution.

Further, the detector 36 can be optionally calibrated to provide a measure of the intensity of the treatment beam propagating towards the intermediate image plane 28. A variety of photodetectors, selected based on the operating wavelength of the treatment light source 12, can be utilized in the practice of the invention. Some examples of such photodetectors can include, but are not limited to, photodiodes, such as a photodiode marketed by Advanced Photonix, Inc. of Camarillo, Calif. under the trade designation SD066-24-21-011.

The exemplary variable spot illuminator further includes a zoom lens system 38 disposed between the intermediate image plane 28 and the treatment plane 14. The zoom lens system 38 can re-image the intermediate image onto the treatment plane with a selected magnification or demagnification (M2). For example, the zoom lens system 38 can transform a disk-like image formed on the intermediate plane onto another disk-like image formed on the treatment plane having a different diameter.

The exemplary zoom lens system 38 includes three lenses 40, 42, and 44, one of which is disposed at a fixed location relative to the intermediate plane and two of which are movable relative to the fixed lens. More specifically, in this exemplary embodiment, the lens 40 is a convergent lens that is fixedly positioned relative to the intermediate image plane 28 while lenses 42 and 44 are movable. The lens 42 is a divergent lens whose distance from the fixed lens 40 can be varied in order to change the size of the image to be formed on the treatment plane at any selected spot size. And the lens 44 is a convergent lens that can be moved to ensure that an image is formed on the treatment plane. In other words, the lens 44 can be moved to compensate for movement of the divergent lens 42 so as to ensure image formation on the treatment plane. In this manner, the spot size of the image formed on the treatment plane can be continuously varied while ensuring that position of the image remains on the treatment plane. That is, variable spot size parfocality condition is achieved. By way of example, the focal lengths of lenses 40, 42 and 44 can be chosen as $F_{40}=25$ mm, $F_{42}=20$ mm and $F_{44}=45$ mm, respectively.

Exemplary values of the focal lengths of the lenses, core diameter of the internal fiber, and magnifications M1 and M2 that can be employed in different applications of a variable spot size illuminator of the invention are provided in Table 1 below.

TABLE 1

| Therapy | Fiber core (μm) | M1 | $F_{30}$ (mm) | $F_{32}$ (mm) | M2 | $F_{40}$ (mm) | $F_{42}$ (mm) | $F_{44}$ (mm) | Spot Size (mm) |
|---|---|---|---|---|---|---|---|---|---|
| PDT | 200 | 5X | 10 | 50 | 1X–6X | 25 | −20 | 45 | 1–6 |
| TTT | 200 | 5X | 10 | 50 | 1X–6X | 25 | −20 | 45 | 1–6 |
| Coagulation | 50 | 5X | 10 | 50 | 1X–6X | 25 | −20 | 45 | 0.25–1.5 |

In this exemplary embodiment, the zoom lens can provide a magnification M2 in a range of 1× to about 6×. Those having ordinary skill in the art will appreciate that the lenses 40, 42, and 44 can be selected such that the zoom lens system would provide other values of magnification.

In this exemplary embodiment, the treatment plane 14 is positioned such that a direction perpendicular to the treatment plane is substantially perpendicular to the direction of the light beam emerging from the zoom lens system 38. Accordingly, a beam splitter 46 is utilized to reflect the light emerging from the zoom lens system 38 to the treatment plane in order to form an image of the intermediate image thereon. A surgeon can observe the treatment area, directly through the beam splitter 46, by employing an observation system 56, as shown in FIG. 1.

In some preferred embodiments of the invention, the zoom lens 38 is designed, as discussed in more detail below, such that the diameter of a light spot formed on a treatment plane differs by less than a selected amount from the diameter of a light spot formed at locations within a selected distance from the treatment plane. In other words, the zoom lens is designed to provide a treatment light spot that exhibits parfocality that is stable with respect to small displacements of the treatment plane, i.e., observation depth of focus parfocality. For example, the zoom lens 38 can be configured such that the diameter of a light spot formed at any location within approximately 5 mm of the treatment plane differs from the diameter of the light spot formed on the treatment plane by less than about 10%.

In addition, the zoom lens 38 can be designed to ensure that the waist of the treatment beam, i.e., the location of minimum cross-sectional diameter of the beam, directed by the zoom lens towards the treatment plane lies close, e.g., within 5 mm of the treatment plane, as the spot size on the treatment plane varies over a selected range, e.g., in a range of about 1 mm to about 6 mm. Such stability of the treatment spot diameter, and consequently the stability of the treatment spot's energy density, relative to displacement about the treatment plane, i.e., observation depth of focus parfocality, provides a number of advantages. For example, as discussed in more detail below, when the variable spot illuminator 10 is utilized for projecting a light spot on a patient's retina, the parfocality provided by the zoom lens 38 prevents drastic changes in the treatment spot's energy density as the patient moves along the illumination axis. This advantageously prevents over-treatment or under-treatment of the illuminated portion of the patient's retina.

In some embodiments of the invention, parfocality can be obtained by optimizing selected parameters of the zoom lens based on maximizing a merit function. Some exemplary optimization parameters can include the radii and focal lengths of the lenses, their respective separations from one another, thickness of each lens, aspheric coefficients associated with the lenses, aperture sizes and wavelengths. The merit function can be defined based on image quality of the light spot at a number of locations including that of the treatment plane, and a number of different spot sizes. The image quality can be defined, for example, as minimum peak-to-valley, or root mean square (RMS), of the spot radius along a horizontal direction (e.g., x direction), or along a vertical direction (e.g., y direction), or as the sum of the radii in the x and y directions (x+y). Alternatively, the image quality can be defined in terms of wavefront error, or modulation transfer function (MTF), or the amount of encircled energy.

The merit function is then globally optimized to obtain values of the zoom lens parameters that provide the best image quality as defined by the merit function. For example, in one embodiment, the merit function is defined based on the image quality of a number of light spots having different sizes on the treatment plane, and on a plane positioned at a selected distance, e.g., 5 mm, away from the treatment plane. One parameter related to the image quality of a light spot on a plane positioned at a distance from the treatment plane can be, for example, the extent to which the spot size on that plane differs from the spot size on the treatment plane. For example, the merit function can be optimized while ensuring that this difference remains below a pre-defined threshold. By way of example, optical design software of Zemax development corporation of San Diego, Calif., U.S.A can be employed to perform the above optimization of the merit function.

With continued reference to FIG. 1, the exemplary variable spot size illuminator 10 further includes a second light source 16 that provides an aiming beam that helps steer the treatment beam onto a desired location on the treatment plane, as described in more detail below. The light source 16 can be, for example, a laser operating at a selected wavelength, for example, at a wavelength in a range of about 630 nm to about 670 nm, such as a laser diode operating at a wavelength of 635 nm. For example, a circular beam laser diode module of Blue Sky Research of Milpitas, California marketed under the trade designation of VersaLase™ can be employed. The intensity of the aiming beam is preferably selected to ensure that the beam intensity is safe for the eye.

The output of the aiming light source 16, which can be in the form of a beam having a substantially circular cross-section, can be optically coupled, for example, via an optical fiber (not shown) or free space propagation, to an axicon 48 that transforms the incident beam into an output beam having a ring-like cross-sectional intensity profile, herein referred to as an annular beam. A convergent lens 50, e.g., a plano-convex lens, forms an image of the annular aiming beam on the intermediate image plane 28.

Figure 3:
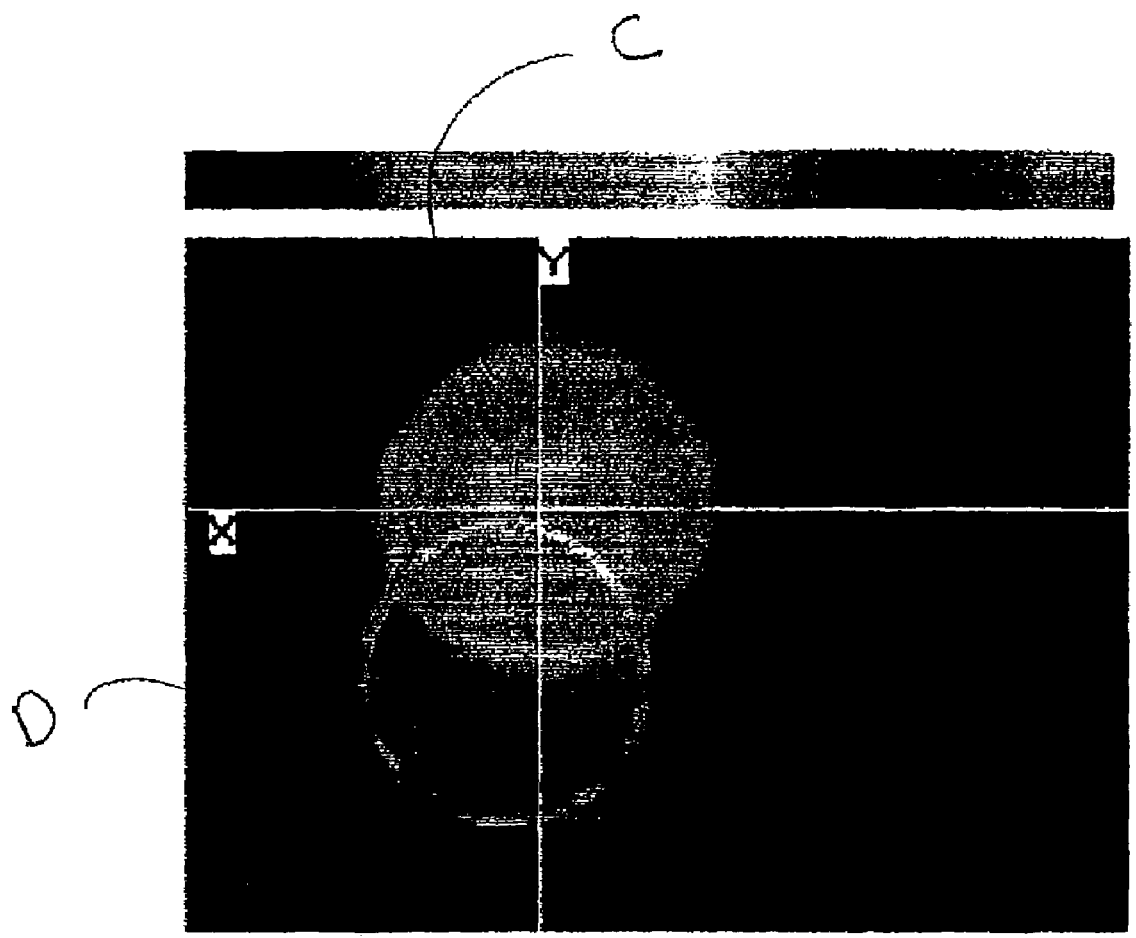
FIG. 3 illustrates cross-sectional views of a treatment beam and an aiming beam, which have been intentionally misaligned for clarity, in the intermediate image plane.

FIG. 3 illustrates exemplary images of a treatment beam C and an annular aiming beam D formed on the intermediate image plane 28. In this exemplary illustration, the treatment beam is intentionally misaligned relative to the annular aiming beam to reveal the ring-like intensity profile of the aiming beam. In normal operation of the variable spot size illuminator 10, however, the treatment beam and the aiming beam are co-axially aligned such that the ring of the aiming beam circumferentially surrounds the treatment beam. Thus, the annular aiming beam advantageously allows undistorted viewing of the treatment area, i.e., the location on the treatment plane where the treatment beam is imaged, for example, under natural white light illumination.

Referring again to FIG. 1, a beam splitter 52 disposed between the focusing lens 50 and the intermediate image plane 28 reflects a portion of the annular aiming beam from its initial propagation direction onto a substantially perpendicular direction towards the intermediate image plane 28. Further, the beam splitter 52 allows transmission of another portion of the aiming beam onto a photodetector 54 that measures the beam's intensity. Typically, the intensity of the reflected portion of the beam is substantially higher than that of the transmitted portion. For example, in this exemplary embodiment, the intensity of the reflected beam is about 95% that of the aiming beam incident on the beam splitter while the intensity of the transmitted beam is only about 5% of the incident beam. To ensure safety of a patient undergoing treatment, in this exemplary embodiment, the treatment beam is only activated when the photodetector 54 detects the aiming beam operating at a safe level. The output signal of the photodetector 54 can be calibrated to report the aiming beam's output power to prevent the aiming beam's power from exceeding a safe level, e.g., not more than 1 mW.

In general, the photo detector 54 is selected to be responsive to the wavelength of the aiming beam. A variety of photo detectors known in the art can be employed for measuring the intensity of the aiming beam. Some examples of suitable photodetectors include, but are not limited to, a photodetector marketed by Advanced Photonix of Camarillo, Calif. under the trade designation SD066-24-21-011.

As illustrated in FIG. 1, in this exemplary embodiment, the aiming beam passes through the beam splitter 34 before reaching the intermediate plane 28. Accordingly, the beamsplitter 34 is selected to be substantially transparent to the aiming beam, that is, substantially transparent to one or more wavelengths corresponding to those of the aiming beam. Moreover, the photodetector 36 utilized for measuring the intensity of the treatment beam can be equipped with a filter, e.g., a bandpass filter, to substantially filter out any portion of the aiming beam that may be reflected by the beam splitter 34 onto the photodetector 36.

Similar to the treatment beam, an image of the aiming beam is initially formed on the intermediate plane 28, and this intermediate image is re-imaged by the zoom lens system 38 onto the treatment plane 14 at a selected magnification. Thus, the annular aiming beam tracks the perimeter of the treatment beam as the zoom lens varies the size of the treatment beam's image, and that of the aiming beam, on the treatment plane. The zoom lens 38 can be designed for achromatic operation to ensure that substantially similar functionality is obtained for both the treatment and the aiming beams.

One application of the above exemplary variable spot size illuminator of the invention relates to laser photocoagulation treatment of a patient's retina. In such an application, the patient's retina forms the treatment plane onto a selected portion of which the treatment beam is directed, for example, with the aid of the aiming beam, to deposit energy, thereby causing coagulation of the local tissue. Photocoagulation can be employed to treat a number of disease conditions of the eye, such as, retinal detachment or diabetic macular edema.

For example, the aiming beam, together with white light illumination of observation system, can be initially employed to observe and select a portion of the patient's retina that requires treatment. The beamsplitter 46 is then adjusted to align the propagation direction of the aiming beam with an axis of observation system (for example, a slit lamp). In order to select different portions of the retina, a surgeon can move and turn the observation system, e.g., slit lamp, and the variable zoom illuminator that can be mechanically attached to the slit lamp in a fixed configuration. Before treating the eye, the treatment beam can be made coaxial with the aiming beam by, for example, observing the images of the two beams on the intermediate image plane, and correcting any observed misalignment by changing the propagation direction of the treatment beam by moving the beam splitter 34. Further, the photodetectors 36 and 54 can be employed to monitor the intensities of the aiming beam and the treatment beam to ensure that they remain within a desired range. Alternatively, or in addition, a sterile contact lens having a negative spherical curvature, which is typically placed on the patient's cornea in such procedures to counter refractive properties of cornea, can be adjusted to select a portion of the retina for observation and treatment.

The selected portion of the retina can then be illuminated by the treatment beam to cause photocoagulation. The annular aiming beam will only outline perimeter of the treatment area and hence will not obscure observation of retina whitening—an important sign of successful coagulation. The treatment beam energy can be delivered, for example, in the form of a plurality of laser pulses, each having a selected energy, at a selected repetition rate. As described above, in many preferred embodiments of the invention, the treatment beam has a flat-top intensity profile that advantageously allows substantially uniform treatment of a selected portion of the retina.

In addition, as discussed above, the zoom lens in a variable spot size illuminator of the invention can be designed such that the size of a light spot formed on a patient's retina varies by less than a few percent (e.g., less than 10 percent) as the patient's head moves approximately mm along the treatment beam during a treatment procedure.

A variable spot size illuminator of the invention can be utilized in ophthalmic surgical procedures other than photocoagulation. For example, such an illuminator can be utilized for performing photodynamic therapy (PDT) in which a drug, commonly referred to as photosensitizer that is inert in the absence of activation, is administered to a patient, and is subsequently activated by light having a selected wavelength. The wavelength of the activating light can be in a range of about 664 nm to about 810 nm, and preferably in a range of about 664 nm to about 732 nm, and more preferably in a range of about 689 nm to about 690 nm, to activate the photosensitizer, which can be, for example, Verteporfin available under trade designation Visudyne from Novartis Pharmaceuticals of Canada.

For example, PDT can be employed for treatment of age-related macular degeneration (AMD) that is a common eye condition that can cause significant visual loss. One form of AMD is caused by growth of abnormal blood vessels under the patient's retina that leak blood and fluid. Photodynamic therapy can be employed to close the leaking blood vessels without damaging the overlying retina. More particularly, an illuminator of the invention can provide a laser light spot with a selected size on the desired portion of the patient's retina to activate a photosensitizer previously administered to the patient, thereby closing the leakage.

In another application, a variable spot size illuminator of the invention can be employed for performing transpupillary thermal therapy (TTT). For example, an illuminator of the invention having a diode laser operating at 810 nm as a radiation source can be employed to heat up large areas of retina to an elevated temperature, e.g., about 49° C.

One advantage of the use of an illuminator of the invention in performing photodynamic or transpupillary thermal therapy is that it provides a relatively uniform light intensity over the illuminated area of the retina, which remains stable over the treatment period, e.g., a few minutes. Further, the treatment spot remains stable relative to small movements of the patient's head, and consequently the patient's retina, in a direction parallel to the beam's propagation. Further, the annular aiming beam does not interfere with the observation of the treatment area under natural white light illumination, which advantageously allows a surgeon to monitor the portion of the retina under treatment for onset of abnormalities, and prevention thereof, during treatment, e.g., retinal damage ("whitening") caused as result of temperature exceeding 49 C.

Figure 4:
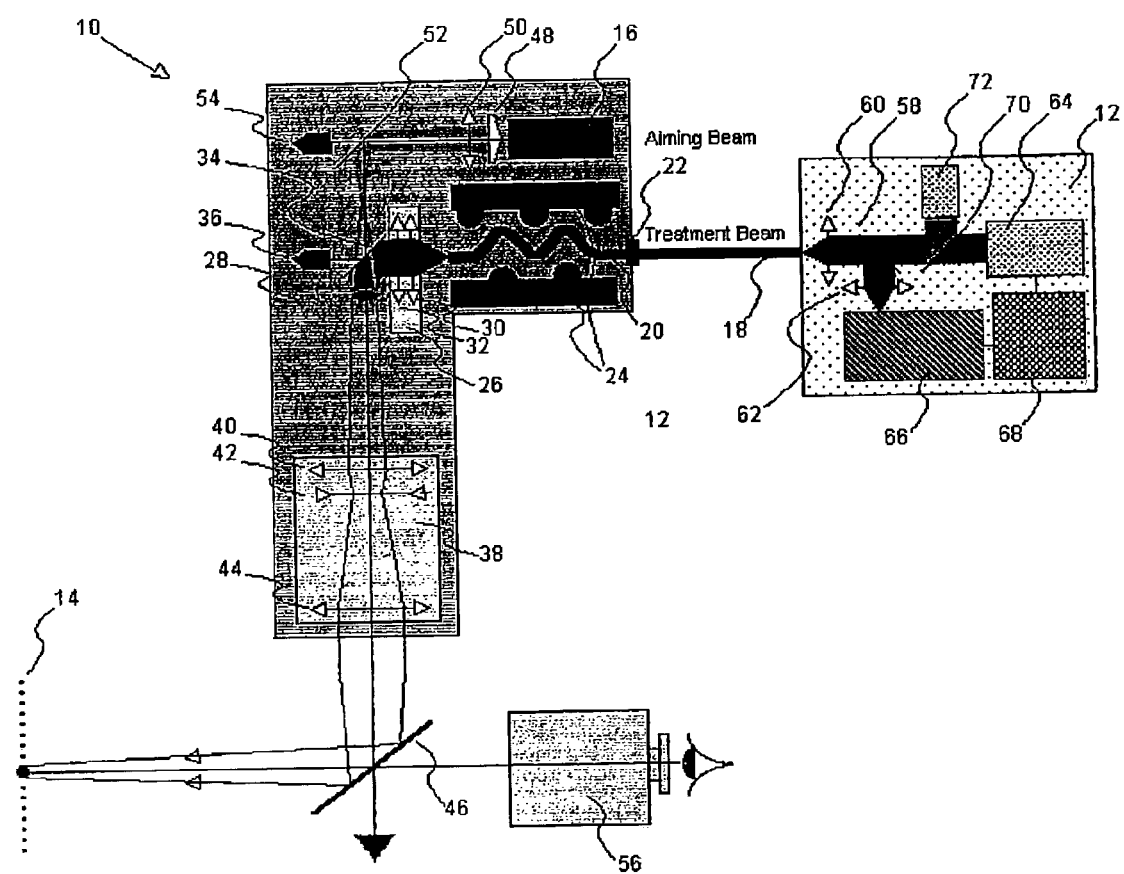
FIG. 4 illustrates an exemplary illuminator of the invention having a feedback system for collecting and analyzing light that emanates from the illuminated treatment spot.

With reference to FIG. 4, in some embodiments of the invention, at least a portion of any radiation originating from the treatment area, for example, scattered, reflected or emitted in response to the treatment radiation, can be collected and analyzed, to provide, for example, real-time feedback regarding the treatment. For example, radiation originating from the treatment area, herein also referred to as feedback radiation, can be directed by the patient's eye lens, and a contact lens if utilized, and the beamplitter 46 into the variable spot size illuminator 10. This feedback radiation can traverse the zoom lens system 38 to be imaged on the intermediate image plane 28. The beam splitter 34 then directs this image of the feedback radiation to the lens system 26 to be imaged onto the output end of the internal optical fiber 20. The internal fiber 20 transmits the feedback radiation to the external fiber 18, which in turn optically couples the radiation to the source 12.

With continued reference to FIG. 4, in this exemplary embodiment, the light source 12 includes an achromatic lens 60 that receives and collimates the feedback radiation. A beamsplitter 58 reflects the collimated feedback radiation onto an achromatic lens 62, which in turn optically couples the feedback radiation to an analyzer 66, e.g., a spectrometer, for analysis. Further, the beamsplitter 58 allows transmission of a treatment beam provided by a laser diode 64 (the treatment beam can be, e.g., p-polarized for better transmission) in a direction opposite to the propagation direction of the feedback radiation towards the achromat 60 and the entrance end of the fiber 18 for delivery onto the treatment plane 14, as described in detail above. In other embodiments, the beamsplitter 58 can be replaced with a grating or a prism or any other suitable optical element for directing the feedback radiation onto the analyzer 66.

In addition, the light source 12 can include a low power probe laser 72. A beam splitter 70 allows transmission of a treatment beam provided by the treatment laser 64 therethrough and directs a probe beam provided by the probe laser 72 onto a path coaxial with the treatment beam such that both the treatment beam and the probe beam illuminate substantially similar portions of the treatment plane, e.g., a patient's retina. The light originated from the illuminated portion of the treatment plane in response to both the treatment beam and the probe beam can be collected as described above. A comparison of the radiation originated from the treatment area in response to the treatment beam relative to the probe beam can provide information regarding certain parameters associated with the illuminated treatment area. For example, as discussed in more detail below, the probe beam's wavelength relative to that of the treatment beam can be selected such that a comparison of the treatment beam's reflectivity relative to the probe beam's reflectivity from the illuminated treatment area can provide information regarding the temperature of the treatment area.

The analyzer 66 can derive various parameters of the feedback radiation, such as, intensity or spectral composition, to generate selected information regarding the illuminated portion of the treatment plane. This information can be displayed, e.g., on a front panel of the illuminator, to provide a real-time feedback and treatment progress report, and can also be utilized for adjusting various parameters of the laser that provides the treatment radiation.

In this exemplary embodiment, a control electronics module 68 provides a feedback path between the analyzer 66 and the laser 64 to allow controlling selected parameters of the laser 64, e.g., intensity, in response to analysis of the feedback radiation. For example, the feedback radiation can be analyzed to extract information regarding the current temperature of the treatment area. For example, the probe laser 72 can be selected to operate at a wavelength, e.g., 690 nm, that is close to the wavelength of the treatment beam, e.g., 810 nm. The analyzer 66 can then analyze the light reflected from the illuminated area of the retina to determine a ratio of the intensity of a spectral component of the reflected light at the probe beam's wavelength relative to that of the spectral component at the treatment beam's wavelength. A black body temperature of the illuminated area can then be extracted from this ratio.

Such real-time temperature information can be utilized, e.g., in transpupillary thermal therapy, to adjust the power of the treatment laser so as to ensure that the temperature of the treatment area will not exceed a selected threshold, e.g., 49 C.

In some applications, the above feedback system can analyze light originating from the treatment area in response to only the treatment beam, i.e., without utilizing the probe beam, to provide selected information regarding the illuminated treatment area. For example, the above feedback system can be employed in photodynamic therapy to monitor near IR (NIR) fluorescence emitted by a PDT photosensitizer when it makes a transition from an excited state, to which it is promoted by an activating treatment radiation, to the ground state so as to monitor photobleaching (photodissociation) of the photosenitizer. It is also well known that a PDT photosensitizer in an excited singlet state can reach an excited triplet state via intersystem crossing. The photosensitizer in the excited triplet state can interact with molecular oxygen to form an excited singlet state of oxygen while transitioning to the ground state. The intensity of NIR phosphorescence of the triplet excited PDT photosentisizer and singlet oxygen can be used to monitor, in real-time, the efficiency of the photodynamic therapy and oxygenation levels of the treatment area. Those having ordinary skill in the art will realize that the above feedback system can be employed for monitoring and/or controlling parameters other than those described above.

Those having ordinary skill in the art will appreciate that a number of modifications can be made to the above embodiments without departing from the scope of the invention. For example, a variety of radiation sources generating radiation having different wavelength can be incorporated in the illuminators of the invention. Further, such illuminators can be utilized in applications other than those enumerated above.

What is claimed is:

1. A variable spot size illuminator comprising
    a) a source of radiation,
    b) a focusing lens system optically coupled to said radiation source to generate an image thereof on an intermediate plane,
    c) a beam splitter disposed between said focusing lens system and said intermediate plane, and
    d) a zoom lens system disposed between said intermediate plane and a treatment plane for forming an image of said intermediate image at a selected size on said treatment plane, said zoom lens having at least one fixed lens and two movable lenses, said movable lenses being adjustably positioned relative to said fixed lens and relative to each other so as to vary a size of the image formed on the treatment plane while ensuring that an image is formed on said treatment plane at any selected size.

2. The variable spot size illuminator of claim 1, wherein said zoom lens system comprises
    a) a focusing convergent lens positioned at a substantially fixed distance relative to said intermediate plane for receiving and refracting light from said intermediate image,
    b) a divergent lens movable relative to said focusing lens for optically receiving light from said focusing convergent lens to generate a plurality of diverging light rays,
    c) a convergent objective lens movable relative to said focusing lens and said divergent lens for imaging said divergent light rays onto the treatment plane so as to form the image on the treatment plane.

3. The variable spot size illuminator of claim 1, wherein the radiation source comprises a treatment laser coupled to said optical fiber to transmit light to said focusing lens system.

4. The variable spot size illuminator of claim 1, wherein said radiation source comprises an optical fiber for illuminating said focusing lens system with a beam of light.

5. The variable spot size illuminator of claim 4, wherein the optical fiber comprises an external optical fiber optically coupled to an internal optical fiber.

6. The variable spot size illuminator of claim 5, wherein said external optical fiber has a diameter in a range of about 100 to about 200 microns.

7. The variable spot size illuminator of claim 6, wherein said internal optical fiber has a diameter in a range of about 200 to about 400 microns.

8. The variable spot size illuminator of claim 5, wherein said beam splitter directs a first portion of said beam along a first direction towards the intermediate image and directs a second portion in a second direction.

9. The variable spot size illuminator of claim 8, wherein said intermediate plane and said zoom lens are positioned relative to one another along said first direction, and said optical fiber illuminates said focusing lens systems along said second direction.

10. The variable sport size illuminator of claim 8, wherein said beam splitter reflects said first portion of the beam received from said second direction onto said first direction, and transmits said second portion onto said detector.

11. The variable spot size illuminator of claim 8, further comprising a detector positioned in said second direction for measuring intensity of said second portion of the beam.

12. The variable spot size illuminator of claim 11, wherein an image of an aiming beam on said intermediate plane is substantially in register with an image of the treatment beam on the intermediate plane.

13. The variable spot size illuminator of claim 12, wherein said image of the aiming beam on said intermediate plane outlines said image of the treatment beam on the intermediate plane.

14. The variable spot size illuminator of claim 12, wherein the image of said annular beam on the intermediate plane circumscribes the image of said treatment beam on the intermediate plane.

15. The variable spot size illuminator of claim 4, further comprising a mode scrambler coupled to said optical fiber to mix energy among a plurality of fiber modes in order to spatially homogenize the beam illuminating the focusing lens system.

16. The variable spot size illuminator of claim 1, further comprising another radiation source for providing a circular aiming beam, and another focusing lens system for imaging said aiming beam onto the intermediate plane.

17. The variable spot size illuminator of claim 16, further comprising a second beam splitter positioned between said another radiation source and said intermediate plane for directing a first portion of the aiming beam along a first direction to the intermediate plane and directing a second portion of the aiming beam to a second direction.

18. The variable spot size illuminator of claim 17, further comprising a second detector positioned along the second propagation direction of the aiming beam to detect said second portion of the aiming beam.

19. The variable spot size illuminator of claim 16, further comprising an axicon positioned between said circular aiming beam light source and said another focusing lens system to generate an annular aiming beam.

* * * * *